United States Patent [19]

Hounsfield et al.

[11] 4,115,697

[45] Sep. 19, 1978

[54] X-RAY TUBE COOLING ARRANGEMENT

[75] Inventors: Godfrey Newbold Hounsfield, Newark; Anthony Michael Williams, Iver, both of England

[73] Assignee: EMI Limited, Hayes, England

[21] Appl. No.: 797,837

[22] Filed: May 17, 1977

[30] Foreign Application Priority Data

Jun. 2, 1976 [GB] United Kingdom ............ 22719/76

[51] Int. Cl.² .................. A61B 6/00; G01N 23/08
[52] U.S. Cl. .................. 250/445 T; 250/419
[58] Field of Search ............ 250/419, 445 T

[56] References Cited

U.S. PATENT DOCUMENTS

| | | | |
|---|---|---|---|
| 1,896,206 | 2/1933 | Smith | 250/419 |
| 1,992,335 | 2/1935 | Tietig | 250/419 |
| 4,001,593 | 1/1977 | Wing et al. | 250/445 T |

Primary Examiner—Alfred E. Smith
Assistant Examiner—T. N. Grigsby
Attorney, Agent, or Firm—Cooper, Dunham, Clark, Griffin & Moran

[57] ABSTRACT

In a computerized tomographic apparatus for radiographic apparatus it has been proposed to orbit a source of X-radiation through several revolutions of the body of the patient. It is desirable to provide cooling to remove generated heat from the X-ray source, this being usually achieved by a cooling fluid such as oil. It is now proposed to provide a closed circuit cooling arrangement, for the source, comprising a circulatory oil path mounted to share in the orbit of the source without external fluid connections. To assist in cooling, the circuit is provided with a radiator and arranged such that, during pauses in the orbit, the radiator is brought to rest in a forced draught from a non-orbiting cooling fan.

9 Claims, 1 Drawing Figure

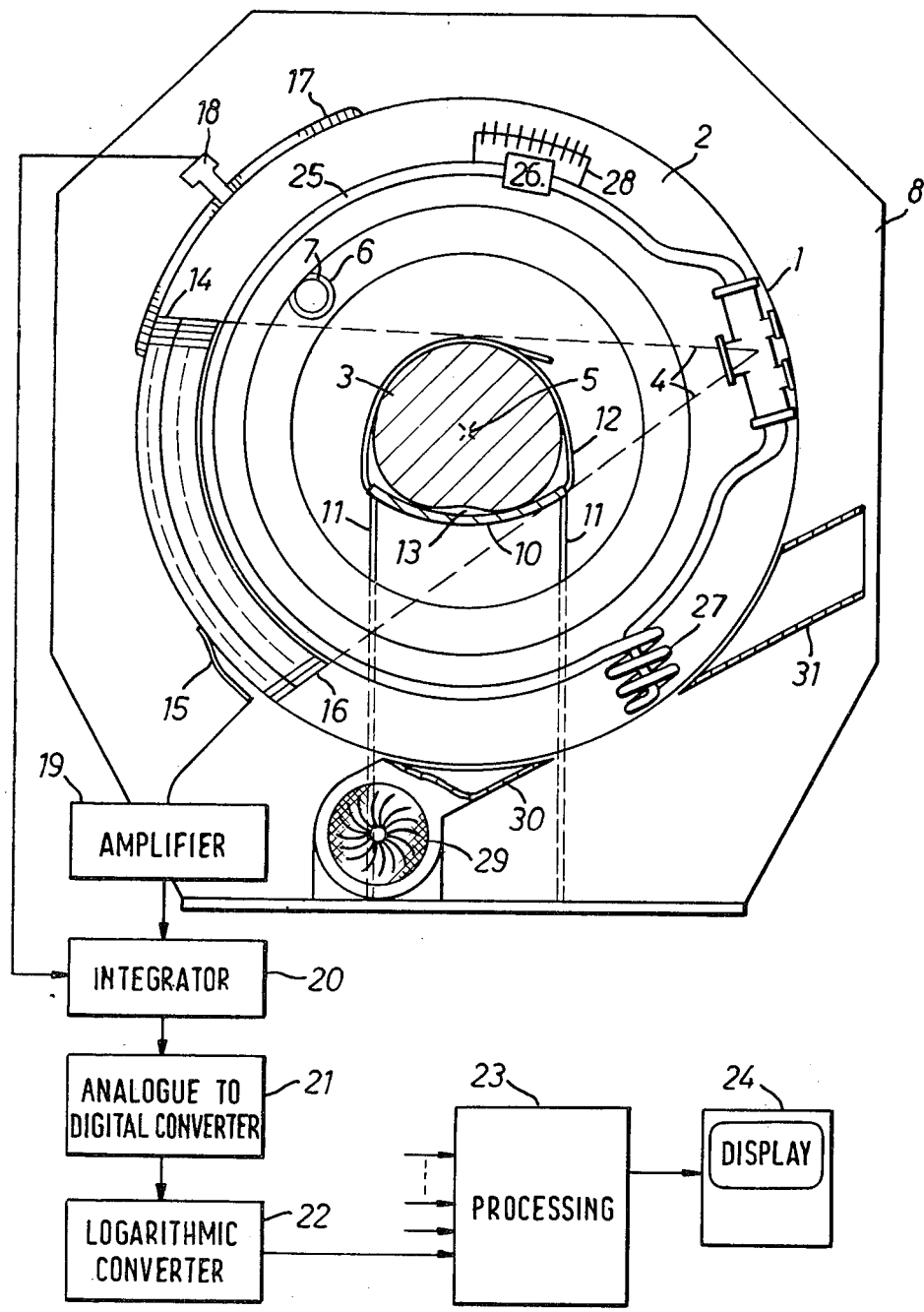

X-RAY TUBE COOLING ARRANGEMENT

This invention relates to the cooling of X-ray apparatus which includes a movable X-ray tube.

In X-ray apparatus of the kind known as computerised tomographic (CAT) apparatus an X-ray tube is arranged to direct radiation through a region, to be examined, of the body of a patient and is moved around the body to direct the radiation therethrough along many different paths. The radiation is detected after passage through the body by one or more detectors and the signals provided by the detectors are processed to provide a representation of the distribution of absorption of the radiation in said region.

In the course of the examination much heat is generated by the X-ray tube and this must be removed if the life of the tube is not to be unduly reduced. It is known to cool X-ray tubes by circulating oil within the tube and externally to some form of oil cooler to remove as much heat as possible. Usually, however, this requires oil connections from the moving parts, including the X-ray tube, to the relatively bulky oil cooler adjacent the apparatus.

It is an object of this invention to provide an alternative technique for cooling a moving X-ray tube.

According to the invention there is provided a radiographic apparatus, for examining a region of the body of a patient, including: a support movable around the body; an X-ray tube mounted on said support to direct radiation through the body; a coolant circuit, connected to said tube and mounted on said support, containing coolant, which can circulate therein, and including a radiative surface at which heat can be removed from the coolant; means for moving the support, and with it the tube and coolant circuit, around the body from a defined rest position, to direct the radiation therethrough along a plurality of different paths thereafter returning to the rest position; and cooling means disposed to direct further coolant at the radiative surface when the support is in said rest position to remove heat from said first mentioned coolant.

In order that the invention may be clearly understood and readily carried into effect an example thereof will now be described with reference to the single FIGURE of the accompanying drawing which shows a CAT apparatus incorporating the invention.

There is shown in the FIGURE an X-ray apparatus which, with the exception of the X-ray tube coolant arrangement, is essentially the same as that described and claimed in U.S. application Ser. No. 481,443 now U.S. Pat. No. 4,035,647 or U.S. application Ser. No. 544,799.

An X-ray tube 1, which is generally of conventional construction, is mounted on an angularly movable ring member 2 so as to irradiate a part 3 of the patient's body. The tube 1 is, in this example, arranged to produce a substantially planar, fan-shaped distribution 4 of X-radiation and the body is positioned so that part 3, which represents a cross-sectional slice over which the absorption is to be evaluated, is in the plane of distribution 4. The angular motion of ring 2 is about an axis 5, which is disposed, in this example, substantially centrally of the body part 3 and is perpendicular to the plane of the distribution 4. The drive for effecting angular motion of ring 2 is an electric motor 6 which drives a gear wheel 7. Wheel 7 cooperates with gear teeth which are not shown but which are formed all around the inner periphery of the ring 2. Motor 6 is mounted on a stationary main frame 8, of the apparatus, with an aperture concentric with the ring 2 and sufficiently large to enable the body to pass through it. The body is supported on a bed 10, which is itself supported at 11, and secured thereto by a strap 12. Packing material 13, which may contain water or particulate or highly viscous material in one or more plastic bags, is placed between the body and the bed 10 in the region of examination so as to reduce the entrapment of air between the body part 13 and bed 10. The material 13 preferably absorbs X-rays to a similar extent as does human tissue.

Ring 2 also supports a bank 14 of detector devices disposed on an arc to receive radiation right across distribution 4 so that each detector receives radiation along an individual beam therein, originating at tube 1. Each detector in the bank 14 typically comprises a scintillator crystal together with a light sensitive element such as a photomultiplier tube or photodiode. The output signals from the detectors are transmitted to a point on the main frame 8. In this example transmission is by one or more brushes 15, cooperating with slip rings formed around the periphery of ring 2. A plurality of collimator plates 16 are also provided to reduce the incidence of scattered radiation on the detectors.

Also around the periphery of member 2 there is formed a graticule 17. The graticule, which is only shown in part, entirely encircles member 2 and comprises opaque markings on a transparent substrate. Main frame 8 carries a photocell unit 18. A light path within 18 is interrupted by the opaque markings and therefore provides timing pulse indicative of the progress of the rotary motion.

Each detector in bank 14 is connected to an independent output channel comprising an amplifier 19, an integrator 20, which is read and reset periodically by the aforementioned timing pulses, an analogue to digital converter circuit 21 and a logarithmic convertor 22. Converter 22 provides a series of pulses each representing the intensity of radiation received along a beam path defined in the course of the rotation by the source and detector motion between two timing pulses. Clearly stationary detectors could be provided on main frame 8 instead of moving ones on ring 2 in which case the procedure would be essentially the same.

All of the logarithmic converter circuits such as 22 feed a processing circuit 23 which is arranged to sort the signals applied thereto into sets relating to parallel beam paths through the body part 3 and to process them according to the technique described and claimed in U.S. Pat. No. 3,924,129 to evaluate the absorption of the radiation in part 3. Alternatively the processing could be by the method described and claimed in U.S. Pat. No. 3,778,614. Preferably the absorption coefficients so evaluated are displayed as a visual display such as a cathode ray tube 24.

As mentioned hereinbefore the apparatus described so far is essentially the same as those described in or operating in accordance with U.S. Pat. No. 3,778,614 and U.S. application Ser. No. 481,443 now U.S. Pat. No. 4,035,647 and U.S. Pat. No. 3,924,129 and U.S. application Ser. No. 544,799 all of which are hereby incorporated herein by reference.

In this example tube 1 is connected to a coolant circulation path to cool the tube, especially the anode by circulation of coolant which is typically oil. The coolant path comprises a conduit 25 forming a closed loop which includes a circulation pump 26 and a radiative surface in the form of a radiator 27. Pump 26 may be associated with a coolant reservoir 28 having fins, if appropriate, for cooling. The coolant may be a known refrigerant which can be intermittently liquid so that the latent heat of evaporation increases the thermal capacity of the system. Pump 26 may be energized by electrical connections to tube 1. Such connections can be further slip rings or other means if desired.

Techniques for closed coolant circulation systems are well known in several arts including refrigeration, heating and internal combustion engine cooling and as such the design of a suitable system will be readily apparent to those skilled in such arts.

The whole coolant circulation system of the present invention rotates along a path around the aperture in ring 2 as the tube 1 is moved in orbit around axis 5 to carry out an examination. As in some circumstances several orbits may be requried a considerable quantity of heat can be generated and this is accumulated in the coolant during the orbits. In this way no flexible or rotation connections are required for coolant.

The accumulated heat is removed by stopping the ring 2 at the end of an examination, at a specific dwell point or rest position such that radiator 27 is in the path of further coolant provided by a forced air blast from a fan 29. This fan, in this example a centrifugal fan fixed in relation to main frame 8, forces air out of a vent 30 shown partly in section, to cross the radiator 27 tangentially to ring 2. Preferably the heated air is collected via a further vent 31, which may be fan assisted, to be removed by suitable means, not shown. Vents 30 and 31 are fixed to main frame 8.

In operation of the X-ray apparatus the X-ray tube 1 is fully energised and generates most heat while a patient is being examined and the ring 2 is in motion. While the patient is being repositioned or removed from the apparatus and another installed, the accumulated heat is removed via radiator 27 since the X-ray tube is producing little or no heat at that time. A typical operating cycle could be 10–30 seconds for X-ray exposure of say eight successive examinations of one patient, during which heat accumulates and 2–5 minutes for patient change during which the system is cooled. A further advantage of the arrangement is that during examination the air blast from fan 29 can be stopped reducing the noise and possible irritation to patients and operating staff.

The reservoir 28 allows the heat for the maximum possible exposure time to be accumulated and then removed as required. Clearly safety devices to prevent over-heating and exposure before sufficient cooling has occurred should be fitted as will be readily apparent to those skilled in the art.

Some cooling occurs during the heating of the coolant, for example due to movement of radiator 27 through the air however the accumulation of heat during movement for subsequent removal provides the main cooling action.

The techniques described above permit the cooling of a movable X-ray tube without the need for flexible coolant connections. Clearly the movement may be other than circular.

In the embodiment described above the radiator provides the greater part of the radiative surface and a separate reservoir is used. Clearly the conduit may itself contain sufficient coolant without the need for a distinct reservoir while the radiative surface may be that of the conduit alone, finned if required. The further coolant air blast may be transverse of the plane of annulus 2 rather than of tangential. The arrangement of the cooling elements shown in the drawing is only exemplary. Clearly other arrangements are possible but it is desirable that the pump be as close as possible to the tube to reduce frictional loss. The second coolant may be a liquid sprayed on to the radiator to evaporate and be pumped away for cooling and recirculation.

Although the X-ray tube has been shown in an open position it will be understood that the ring 2 will normally be in an approximately annular shield and not visible to the patient. This annular shield may conveniently provide a closed system on which vents 30 and 31 are mounted thus protecting the patient from any air flow or heat generated.

What we claim is:

1. A radiographic apparatus, for examining a region of the body of a patient, including: a support movable around the body; an X-ray tube mounted on said support to direct radiation through the body; a coolant circuit, connected to said tube and mounted on said support, containing coolant, which can circulate therein, and including a radiative surface at which heat can be removed from the coolant; means for moving the support, and with it the tube and coolant circuit, around the body from a defined rest position, to direct the radiation therethrough along a plurality of different paths thereafter returning to the rest position; and cooling means disposed to direct further coolant at the radiative surface when the support is in said rest position to remove heat from said first mentioned coolant.

2. A radiographic apparatus according to claim 1 in which the means for moving comprises means for moving the support through a plurality of revolutions about the body before returning to the rest position.

3. A radiographic apparatus according to claim 1 in which the coolant circuit includes a coolant reservoir.

4. A radiographic apparatus according to claim 1 in which the first mentioned coolant is intermittently liquid to utilize the latent heat of change of state to increase the thermal capacity thereof.

5. A radiographic apparatus according to claim 1 in which said cooling means comprises means directing an air blast at said radiative surface.

6. A radiographic apparatus according to claim 5 in which the cooling means is a fan.

7. A radiographic apparatus according to claim 5 wherein the cooling means includes means for directing the air blast tangentially to the locus of motion of the radiative surface.

8. A radiographic apparatus according to claim 1 in which the radiative surface comprises a coil or loop in the coolant circuit.

9. A radiographic apparatus according to claim 1 wherein the coolant circuit mounted on said support movable around the body comprises a closed coolant circuit.

* * * * *